(12) United States Patent
Kautz et al.

(10) Patent No.: US 7,423,046 B2
(45) Date of Patent: *Sep. 9, 2008

(54) 3-HYDROXY-6-PHENYLPHENANTHRIDINES AS PDE-4 INHIBITORS

(75) Inventors: Ulrich Kautz, Allensbach (DE); Beate Schmidt, Allensbach (DE)

(73) Assignee: Nycomed GmbH, Constance (DE)

( * ) Notice: Subject to any disclaimer, the term of this patent is extended or adjusted under 35 U.S.C. 154(b) by 464 days.

This patent is subject to a terminal disclaimer.

(21) Appl. No.: 10/524,820

(22) PCT Filed: Aug. 29, 2003

(86) PCT No.: PCT/EP03/09601

§ 371 (c)(1),
(2), (4) Date: Feb. 18, 2005

(87) PCT Pub. No.: WO2004/019945

PCT Pub. Date: Mar. 11, 2004

(65) Prior Publication Data

US 2005/0239818 A1    Oct. 27, 2005

(30) Foreign Application Priority Data

Aug. 29, 2002  (EP) ................. 02019336

(51) Int. Cl.
C07D 221/10   (2006.01)
A61K 31/473   (2006.01)
(52) U.S. Cl. ..................... 514/297; 546/101
(58) Field of Classification Search ............. 546/101; 514/297
See application file for complete search history.

(56) References Cited

U.S. PATENT DOCUMENTS

| | | |
|---|---|---|
| 6,121,279 A | 9/2000 | Gutterer |
| 6,127,378 A | 10/2000 | Gutterer |
| 6,191,138 B1 | 2/2001 | Gutterer |
| 6,306,869 B1 | 10/2001 | Flockerzi |
| 6,410,551 B1 | 6/2002 | Gutterer |
| 6,476,025 B1 | 11/2002 | Gutterer |
| 2005/0239817 A1* | 10/2005 | Kautz et al. ........ 514/298 |
| 2007/0191414 A1* | 8/2007 | Kautz ................. 514/285 |

FOREIGN PATENT DOCUMENTS

| | | | |
|---|---|---|---|
| EP | 0 490 823 A1 | 6/1992 | |
| WO | 97/28131 A1 | 8/1997 | |
| WO | 97/35854 A1 | 10/1997 | |
| WO | 99/05111 A1 | 2/1999 | |
| WO | 99/05112 A1 | 2/1999 | |
| WO | 99/05113 A1 | 2/1999 | |
| WO | 99/57118 A1 | 11/1999 | |
| WO | 00/42017 A1 | 7/2000 | |
| WO | 00/42018 A1 | 7/2000 | |
| WO | 00/42019 A1 | 7/2000 | |
| WO | 00/42020 A1 | 7/2000 | |
| WO | 00/42034 A1 | 7/2000 | |
| WO | 02/05616 A1 | 1/2002 | |
| WO | 02/06238 A1 | 1/2002 | |
| WO | 02/06270 A1 | 1/2002 | |
| WO | 02/066476 A1 | 8/2002 | |
| WO | 2004/018431 A2 | 3/2004 | |
| WO | 2004/019944 A1 | 3/2004 | |
| WO | 2005/077906 A1 | 8/2005 | |
| WO | 2005/084104 A2 | 9/2005 | |
| WO | 2005/085203 A1 | 9/2005 | |
| WO | 2005/085225 A1 | 9/2005 | |
| WO | 2005/087744 A1 | 9/2005 | |
| WO | 2005/087745 A1 | 9/2005 | |
| WO | 2005/090311 A1 | 9/2005 | |
| WO | 2006/092422 A1 | 9/2006 | |

OTHER PUBLICATIONS

Dorwald F. A. Side Reactions in Organic Synthesis, 2005, Wiley: VCH, Weinheim p. IX of Preface.*
West, Anthony R., Solid State Chemistry and its Applications, Wiley, New York, 1988, pp. 358 & 365.*
U.S. Appl. No. 12/000,710, filed Dec. 2007, Ulrich Kautz.*
"Souness, J.E., "Immunosuppressive and anti-inflammatory effects of cyclic AMP phosphodiesterase (PDE) type 4 inhibitors". *Immunopharmacology*, vol. 47, p. 127-162, 2000".
"Dyke, H.J., "Update on the therapeutic potential of PDE4 inhibitors". *Expert Opinion on Investigational Drugs*, vol. 11, No. 1, p. 1-13, 2002".
Montana, J., "Chapter 5. Phosphodiesterase 4 Inhibitors". *Annual Reports Med Chem*, vol. 36, p. 47-56, 2001.
"Schmidt, B.J., "The phosphodiesterase 4 inhibitor roflumilast is effective in the treatment of allergic rhinitis". *Allergy Clin Immunol*, vol. 108, p. 530-536, 2001".

* cited by examiner

*Primary Examiner*—Rita J Desai
(74) *Attorney, Agent, or Firm*—The Nath Law Group; Joshua B. Goldberg; Sheldon M. McGee

(57) ABSTRACT

Compounds of formula (I), in which R1, R2, R3, R4, R5, R6 and R7 have the meaning indicated in the description, are novel effective PDE4 inhibitors.

9 Claims, No Drawings

SEQUENCE LISTING

```
<160> NUMBER OF SEQ ID NOS: 2

<210> SEQ ID NO 1
<211> LENGTH: 22
<212> TYPE: DNA
<213> ORGANISM: Homo sapiens

<400> SEQUENCE: 1
gccagcgtgc aaataatgaa gg                                              22

<210> SEQ ID NO 2
<211> LENGTH: 21
<212> TYPE: DNA
<213> ORGANISM: Homo sapiens

<400> SEQUENCE: 2 agaggggat tatgtatcca c                                                21
```

3-HYDROXY-6-PHENYLPHENANTHRIDINES AS PDE-4 INHIBITORS

FIELD OF APPLICATION OF THE INVENTION

The invention relates to novel 3-hydroxy-6-phenylphenanthridines, which are used in the pharmaceutical industry for the production of pharmaceutical compositions.

KNOWN TECHNICAL BACKGROUND

The international applications WO 97/28131 (=U.S. Pat. No. 6,191,138), WO 97/35854 (=U.S. Pat. No. 6,127,378), WO 99/05113 (=U.S. Pat. No. 6,121,279), WO99/05111 (=U.S. Pat. No. 6,410,551), WO 00/42018, WO 00/42020, WO 02/05616 and WO 02/06238 describe 6-phenylphenanthridines as PDE4 inhibitors.

DESCRIPTION OF THE INVENTION

It has now been found that the novel 3-hydroxy-6-phenylphenanthridines described in greater detail below differ from the previously known 6-phenophenanthridines by unanticipated and sophisticated structural alterations and have surprising and particularly advantageous properties.

The invention thus relates to compounds of the formula I,

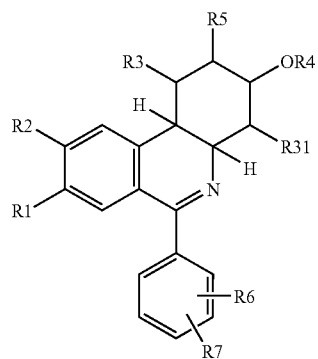

in which
R1 is hydroxyl, 1-4C-alkoxy, 3-7C-cycloalkoxy, 3-7C-cycloalkylmethoxy or completely or predominantly fluorine-substituted 1-4C-alkoxy,
R2 is hydroxyl, 1-4C-alkoxy, 3-7C-cycloalkoxy, 3-7C-cycloalkylmethoxy or completely or predominantly fluorine-substituted 1-4C-alkoxy,
or in which
R1 and R2 together are a 1-2C-alkylenedioxy group,
R3 is hydrogen or 1-4C-alkyl,
R31 is hydrogen or 1-4C-alkyl,
R4 is hydrogen, 1-4C-alkyl, completely or predominantly fluorine-substituted 1-4C-alkyl, 1-4C-alkoxy-1-4C-alkyl, hydroxy-2-4C-alkyl or 1-7C-alkylcarbonyl,
R5 is hydrogen or 1-4C-alkyl,
R6 is hydrogen, 1-4C-alkyl, trifluoromethyl, 1-4C-alkoxy, completely or predominantly fluorine-substituted 1-4C-alkoxy, 3-7C-cycloalkoxy, 3-7C-cycloalkylmethoxy, halogen, nitro, cyano, hydroxyl, 1-4C-alkylcarbonyloxy, amino, mono- or di-1-4C-alkylamino, phenyl, phenyl-1-4C-alkyl, 1-4C-alkylcarbonylamino, phenoxy or C(O)OR61, wherein
R61 is hydrogen, 1-7C-alkyl, 3-7C-cycloalkyl or 3-7C-cycloalkylmethyl,
R7 is hydrogen, 1-4C-alkyl, hydroxyl, halogen, 1-4C-alkoxy, completely or predominantly fluorine-substituted 1-4C-alkoxy, 3-7C-cycloalkoxy, 3-7C-cycloalkylmethoxy or C(O)OR61, and the salts, the N-oxides and the salts of the N-oxides of these compounds.

1-4C-Alkyl represents a straight-chain or branched alkyl radical having 1 to 4 carbon atoms. Examples which may be mentioned are the butyl, isobutyl, sec-butyl, tert-butyl, propyl, isopropyl and preferably the ethyl and methyl radicals.

1-7C-Alkyl represents a straight-chain or branched alkyl radical having 1 to 7 carbon atoms. Examples which may be mentioned are the heptyl, isoheptyl(5-methylhexyl), hexyl, isohexyl(4-methylpentyl), neohexyl (3,3-dimethylbutyl), pentyl, isopentyl(3-methylbutyl), neopentyl(2,2-dimethylpropyl), butyl, isobutyl, sec-butyl, tert-butyl, propyl, isopropyl, ethyl or methyl radicals.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

3-7C-Cycloalkoxy represents cyclopropyloxy, cyclobutyloxy, cyclopentyloxy, cyclohexyloxy and cycloheptyloxy, of which cyclopropyloxy, cyclobutyloxy and cyclopentyloxy are preferred.

3-7C-Cycloalkylmethoxy represents cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

As completely or predominantly fluorine-substituted 1-4C-alkoxy, for example, the 2,2,3,3,3-pentafluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy radicals may be mentioned. "Predominantly" in this connection means that more than half of the hydrogen atoms of the 1-4C-alkoxy radicals are replaced by fluorine atoms.

As completely or predominantly fluorine-substituted 1-4C-alkyl, for example, the 2,2,3,3,3-pentafluoropropyl, the perfluoroethyl, the 1,2,2-trifluoroethyl, in particular the 1,1,2,2-tetrafluoroethyl, the 2,2,2-trifluoroethyl, the trifluoromethyl and preferably the difluoromethyl radicals may be mentioned. "Predominantly" in this connection means that more than half of the hydrogen atoms of the 1-4C-alkyl radicals are replaced by fluorine atoms.

1-2C-Alkylenedioxy represents, for example, the methylenedioxy [—O—$CH_2$—O—] and the ethylenedioxy [—O—$CH_2$—$CH_2$—O—] radicals.

1-4C-Alkoxy-1-4C-alkyl represents one of the abovementioned 1-4C-alkyl radicals, which is substituted by one of the abovementioned 1-4C-alkoxy radicals. Examples which may be mentioned are the methoxymethyl, the methoxyethyl and the isopropoxyethyl radicals, particularly the 2-methoxyethyl and the 2-isopropoxyethyl radicals.

1-4C-Alkylcarbonyl represents a radical which, in addition to the carbonyl group, contains one of the abovementioned 1-4C-alkyl radicals. An example which may be mentioned is the acetyl radical.

1-7C-Alkylcarbonyl represents a radical which, in addition to the carbonyl group, contains one of the abovementioned 1-7C-alkyl radicals. Examples which may be mentioned are the acetyl, propionyl, butanoyl and hexanoyl radicals.

Hydroxy-2-4C-alkyl represents 2-4C-alkyl radicals, which are substituted by a hydroxyl group. Examples which may be mentioned are the 2-hydroxyethyl and the 3-hydroxypropyl radicals.

In addition to the nitrogen atom, mono- or di-1-4C-alkylamino radicals contain one or two of the above-mentioned 1-4C-alkyl radicals. Di-1-4C-alkylamino is preferred and here, in particular, dimethyl-, diethyl- or diisopropylamino.

Halogen within the meaning of the invention is bromine, chlorine or fluorine.

3-7C-Cycloalkyl represents cyclopropyl, cyclobutyl, cyclopentyl, cyclohexyl and cycloheptyl, of which cyclopropyl, cyclobutyl and cyclopentyl are preferred.

3-7C-Cycloalkylmethyl represents a methyl radical which is substituted by one of the abovementioned 3-7C-cycloalkyl radicals. Preferably, the 3-5C-cycloalkylmethyl radicals cyclopropylmethyl, cyclobutylmethyl and cyclopentylmethyl may be mentioned.

Phenyl-1-4C-alkyl represents one of the abovementioned, phenyl-substituted 1-4C-alkyl radicals. Examples which may be mentioned are the phenethyl and the benzyl radicals.

1-4C-Alkylcarbonyloxy represents a carbonyloxy group to which one of the abovementioned 1-4C-alkyl radicals is bonded. An example which may be mentioned is the acetoxy radical [$CH_3C(O)$—O—].

1-4C-Alkylcarbonylamino represents an amino radical which is substituted by one of the abovementioned 1-4C-alkylcarbonyl radicals. An example which may be mentioned is the acetamido radical [$CH_3C(O)$—NH—].

Exemplary phenyl radicals substituted by R6 and R7 which may be mentioned are the radicals 4-acetamidophenyl, 3-acetamidophenyl, 4-acetoxyphenyl, 3-aminophenyl, 4-aminophenyl, 2-bromophenyl, 4-bromophenyl, 2-chlorophenyl, 3-chlorophenyl, 4-chlorophenyl, 3-bromophenyl, 2,3-dichlorophenyl, 2,4-dichlorophenyl, 2-chloro-4-nitrophenyl, 4-diethylamino-2-methylphenyl, 4-methoxyphenyl, 3-methoxyphenyl, 2-chloro-5-nitrophenyl, 4-chloro-3-nitrophenyl, 2,6-dichlorophenyl, 3,5-dichlorophenyl, 2,5-dichlorophenyl, 2,6-dibromophenyl, 2-cyanophenyl, 3-cyanophenyl, 4-cyanophenyl, 4-di-ethylaminophenyl, 4-dimethylaminophenyl, 2-fluorophenyl, 4-fluorophenyl, 3-fluorophenyl, 2,4-difluorophenyl, 2,6-difluorophenyl, 2-chloro-6-fluorophenyl, 2-fluoro-5-nitrophenyl, 2-hydroxyphenyl, 3-hydroxyphenyl, 3,4-dichlorophenyl, 4-hydroxyphenyl, 4-hydroxy-3-methoxyphenyl, 2-hydroxy-4-methoxyphenyl, 2,4-dihydroxyphenyl, 2-methoxyphenyl, 2,3-dimethoxyphenyl, 3,4-dimethoxyphenyl, 2,4-dimethoxyphenyl, 3-dimethylaminophenyl, 2-dimethylaminophenyl, 2-methylphenyl, 3-methylphenyl, 4-methylphenyl, 2-chloro-6-methylphenyl, 4-methyl-3-nitrophenyl, 2,4-dimethylphenyl, 2,6-dimethylphenyl, 2,3-dimethylphenyl, 2-nitrophenyl, 3-nitrophenyl, 4-nitrophenyl, 4-ethoxyphenyl, 2-trifluoromethylphenyl, 4-trifluoromethylphenyl, 3-trifluoromethylphenyl, 4-benzylphenyl, 4-biphenyl, 4-trifluoromethoxyphenyl, 3-trifluoromethoxyphenyl, 2-trifluoromethoxyphenyl, 3-cyclopentyloxyphenyl, 4-cyclopentyloxyphenyl, 4-cyclohexyoxyphenyl, 3-cyclohexyloxyphenyl, 3-cyclopropymethoxyphenyl, 4-cyclopropylmethoxyphenyl, 3-cyclopropylmethoxy-4-methoxyphenyl, 3-cyclopropylmethoxy-4-difluoromethoxyphenyl, 3-cyclopropylmethoxy-4-ethoxyphenyl, 4-cyclopropylmethoxy-3-methoxyphenyl, 3-cyclopropylmethoxy-5-methoxyphenyl, bis-3,4-cyclopropylmethoxyphenyl, bis-3,5-cyclopropylmethoxyphenyl, 3,4-dicyclopentyloxyphenyl, 3-cyclopentyloxy-4-methoxyphenyl, 4-cyclopentyloxy-3-methoxyphenyl, 3-cyclopropylmethoxy-4-cyclopentyloxyphenyl, 3-cyclopentyloxy-5-methoxyphenyl, 4-cyclopropylmethoxy-3-cyclopentyloxyphenyl, 3-cyclobutyloxy-4-methoxyphenyl, 3-cyclopropylmethoxy-4-acetylaminophenyl, 4-carboxyphenyl, 4-methoxycarbonylphenyl, 4-ethoxycarbonylphenyl, 4-isopropoxycarbonylphenyl, 3-carboxyphenyl, 3-methoxycarbonylphenyl, 3-ethoxycarbonylphenyl, 3-isopropoxycarbonylphenyl, 4-methoxycarbonyl-3-methylphenyl, 3-chloro-4-methoxycarbonylphenyl, 3-bromo-4-methoxycarbonylphenyl, 3-fluoro-4-methoxycarbonylphenyl, 3-hydroxy-4-methoxycarbonylphenyl, 2-chloro-4-methoxycarbonylphenyl, 2-bromo-4-methoxycarbonylphenyl, 2-fluoro-4-methoxycarbonylphenyl, 2-methoxy-4-methoxycarbonylphenyl, 4-methoxycarbonyl-2-methylcarbonylphenyl, 4-fluoro-3-methoxycarbonylphenyl, 4-ethoxy-3-methoxycarbonylphenyl, 4-methoxy-3-methoxycarbonylphenyl, 4-isopropoxy-3-methoxycarbonylphenyl, 3-methoxycarbonyl-4-methylphenyl, 5-tert-butyl-3-methoxycarbonylphenyl, 3-methoxycarbonyl-5-methylphenyl, 3-bromo-5-methoxycarbonylphenyl, 3-chloro-5-methoxycarbonylphenyl, 3-methoxy-5-methoxycarbonylphenyl, 3-acetoxy-4-methoxycarbonylphenyl, 4-methoxycarbonyl-2-nitrophenyl, 4-methoxycarbonyl-2-phenylphenyl, 2-cyano-4-methoxycarbonylphenyl, 4-acetoxy-3-methoxycarbonylphenyl, 3-methoxycarbonyl-4-nitrophenyl, 3-methoxycarbonyl-5-phenylphenyl, 5-cyano-3-methoxycarbonylphenyl or 5-methoxycarbonyl-3-nitrophenyl, 4-methoxy-3-propoxy-phenyl, 4-butoxyphenyl, 4-difluoromethoxyphenyl, 3-difluoromethoxyphenyl, 3,4-bis-difluoromethoxyphenyl, 4-(1,1,2,2-tetrafluoroethoxy)-phenyl, 3-fluoro-4-methoxyphenyl or 4-phenoxyphenyl.

Possible salts for compounds of the formula I—depending on substitution—are all acid addition salts or all salts with bases. Particular mention may be made of the pharmacologically tolerable salts of the inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, it being possible to employ the acids in salt preparation—depending on whether a mono- or polybasic acid is concerned and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Pharmacologically intolerable salts which can initially be obtained, for example, as process products in the preparation of the compounds according to the invention on an industrial scale are converted into pharmacologically tolerable salts by processes known to the person skilled in the art.

It is known to the person skilled in the art that the compounds according to the invention and their salts, when they are isolated, for example, in crystalline form, can contain various amounts of solvents. The invention therefore also comprises all solvates and in particular all hydrates of the compounds of the formula I, and also all solvates and in particular all hydrates of the salts of the compounds of the formula I.

The substituents R6 and R7 of compounds of formula I can be attached in the ortho, meta or para position with respect to the binding position in which the 6-phenyl ring is bonded to the phenanthridine ring system, whereby preference is given to the attachement in the meta or, particularly, in the para position.

An embodiment (embodiment a) of the invention are compounds of the formula I in which
R1 is 1-2C-alkoxy, 3-5C-cycloalkoxy, 3-5C-cycloalkylmethoxy or completely or predominantly fluorine-substituted 1-2C-alkoxy,
R2 is 1-2C-alkoxy, 3-5C-cycloalkoxy, 3-5C-cycloalkylmethoxy or completely or predominantly fluorine-substituted 1-2C-alkoxy,
R3 is hydrogen,
R31 is hydrogen,
R4 is hydrogen, 1-4C-alkyl, 1-2C-alkoxy-2-4C-alkyl or 1-7C-alkylcarbonyl,
R5 is hydrogen,
R6 is 1-4C-alkyl, 1-4C-alkoxy, completely or predominantly fluorine-substituted 1-4C-alkoxy, 3-7C-cycloalkylmethoxy, halogen, nitro, cyano, hydroxyl, 1-4C-alkylcarbonyloxy, mono- or di-1-4C-alkylamino, 1-4C-alkylcarbonylamino, phenoxy or C(O)OR61, wherein
R61 is hydrogen or 1-7C-alkyl,
R7 is hydrogen, halogen, 1-4C-alkoxy, completely or predominantly fluorine-substituted 1-4C-alkoxy or 3-7C-cycloalkylmethoxy, and the salts, the N-oxides and the salts of the N-oxides of these compounds.

Compounds of embodiment a, which are to be emphasized, are those compounds of the formula I in which
R1 is 1-2C-alkoxy or completely or predominantly fluorine-substituted 1-2C-alkoxy,
R2 is 1-2C-alkoxy or completely or predominantly fluorine-substituted 1-2C-alkoxy,
R3 is hydrogen,
R31 is hydrogen,
R4 is hydrogen, 1-4C-alkyl, 1-2C-alkoxyethyl or 1-7C-alkylcarbonyl,
R5 is hydrogen,
R6 is 1-4C-alkyl, 1-4C-alkoxy, completely or predominantly fluorine-substituted 1-4C-alkoxy, 3-7C-cycloalkylmethoxy, halogen, nitro, cyano, hydroxyl, 1-4C-alkylcarbonyloxy, mono- or di-1-4C-alkylamino, 1-4C-alkylcarbonylamino, phenoxy or C(O)OR61, wherein
R61 is hydrogen or 1-7C-alkyl,
R7 is hydrogen, halogen, 1-4C-alkoxy, completely or predominantly fluorine-substituted 1-4C-alkoxy or 3-7C-cycloalkylmethoxy, and the salts, the N-oxides and the salts of the N-oxides of these compounds.

Compounds of embodiment a, which are in particular to be emphasized, are those compounds of the formula I in which
R1 is methoxy or difluoromethoxy,
R2 is methoxy, difluoromethoxy or ethoxy,
R3 is hydrogen,
R31 is hydrogen,
R4 is hydrogen or acetyl,
R5 is hydrogen,
R6 is cyano or cyclopropylmethoxy,
R7 is hydrogen or cyclopropylmethoxy, and the salts, the N-oxides and the salts of the N-oxides of these compounds.

Compounds of embodiment a, which are in more particular to be emphasized, are those compounds of the formula I in which
R1 is methoxy,
R2 is methoxy,
R3 is hydrogen,
R31 is hydrogen,
R4 is hydrogen or acetyl,
R5 is hydrogen,
R6 is cyano or cyclopropylmethoxy,
R7 is hydrogen or cyclopropylmethoxy, and the salts, the N-oxides and the salts of the N-oxides of these compounds.

A further embodiment (embodiment b) of the invention are compounds of the formula I in which
R1 is 1-2C-alkoxy, 3-5C-cycloalkoxy, 3-5C-cycloalkylmethoxy or completely or predominantly fluorine-substituted 1-2C-alkoxy,
R2 is 1-2C-alkoxy, 3-5C-cycloalkoxy, 3-5C-cycloalkylmethoxy or completely or predominantly fluorine-substituted 1-2C-alkoxy,
R3 is hydrogen,
R31 is hydrogen,
R4 is hydrogen, 1-4C-alkyl, completely or predominantly fluorine-substituted 1-2C-alkyl, 1-2C-alkoxy-1-2C-alkyl, 2-hydroxyethyl or 1-7C-alkylcarbonyl,
R5 is hydrogen,
R6 is hydrogen, 1-4C-alkyl, 1-4C-alkoxy, completely or predominantly fluorine substituted 1-2C-alkoxy, 3-7C-cycloalkoxy, 3-7C-cycloalkylmethoxy, halogen, nitro, amino, mono- or di-1-4C-alkylamino, 1-4C-alkylcarbonylamino or C(O)OR61, wherein
R61 is hydrogen, 1-4C-alkyl, 3-5C-cycloalkyl or 3-5C-cycloalkylmethyl,
R7 is hydrogen, 1-4C-alkyl, halogen, 1-4C-alkoxy, completely or predominantly fluorine-substituted 1-2C-alkoxy, 3-7C-cycloalkoxy or 3-7C-cycloalkylmethoxy, and the salts, the N-oxides and the salts of the N-oxides of these compounds.

Compounds of embodiment b, which are to be emphasized, are those compounds of the formula I in which
R1 is 1-2C-alkoxy,
R2 is 1-2C-alkoxy,
R3 is hydrogen,
R31 is hydrogen,
R4 is hydrogen, 1-4C-alkyl, 1-2C-alkoxy-1-2C-alkyl or 1-7C-alkylcarbonyl,
R5 is hydrogen,
R6 is 1-4C-alkoxy, completely or predominantly fluorine-substituted 1-2C-alkoxy, 3-7C-cycloalkoxy or 3-7C-cycloalkylmethoxy,
R7 is hydrogen, 1-4C-alkoxy, completely or predominantly fluorine-substituted 1-2C-alkoxy, 3-7C-cycloalkoxy or 3-7C-cycloalkylmethoxy, and the salts, the N-oxides and the salts of the N-oxides of these compounds.

Compounds of embodiment b, which are particularly to be emphasized, are those compounds of the formula I in which
R1 is 1-2C-alkoxy,
R2 is 1-2C-alkoxy,
R3 is hydrogen,
R31 is hydrogen, R4 is hydrogen or 1-4C-alkylcarbonyl,
R5 is hydrogen,
R6 is 3-7C-cycloalkylmethoxy,
R7 is 3-7C-cycloalkylmethoxy, and the salts, the N-oxides and the salts of the N-oxides of these compounds.

Preferred compounds of embodiment b are those compounds of the formula I in which
R1 is methoxy,
R2 is methoxy,
R3 is hydrogen,
R31 is hydrogen,
R4 is hydrogen or acetyl,
R5 is hydrogen,
R6 is cyclopropylmethoxy,
R7 is cyclopropylmethoxy, and the salts, the N-oxides and the salts of the N-oxides of these compounds.

Preferred exemplary compounds of the formula I are
(±)-acetic acid (3RS,4aRS,10bRS)-6-(3,4-bis-cyclopropylmethoxyphenyl)-8,9-dimethoxy-(1,2,3,4,4a,10b)-hexahydrophenanthridin-3-yl ester,
(±)-acetic acid (3SR,4aRS,10bRS)-6-(3,4-bis-cyclopropylmethoxyphenyl)-8,9-dimethoxy-(1,2,3,4,4a,10b)-hexahydrophenanthridin-3-yl ester,
(±)-(3RS,4aRS,10bRS)-6-(3,4-bis-cyclopropylmethoxyphenyl)-8,9-dimethoxy-(1,2,3,4,4a,10b)-hexahydrophenanthridin-3-ol,
(±)-(3SR,4aRS,10bRS)-6-(3,4-bis-cyclopropylmethoxyphenyl)-8,9-dimethoxy-1,2,3,4,4a,10b-hexahydrophenanthridin-3-ol,
(±)-acetic acid (3SR,4aRS,10bRS-6-(4-cyanophenyl)-8,9-dimethoxy-(1,2,3,4,4a,10b)-hexahydrophenanthridin-3-yl ester, and
(±)-4-((3SR,4aRS,10bRS)-3-hydroxy-8,9-dimethoxy-(1,2,3,4,4a,10b)-hexahydrophenanthridin-6-yl)-benzonitrile, and the salts, the N-oxides and the salts of the N-oxides of these compounds.

A special embodiment of the compounds of the present invention include those compounds of the formula I in which R1 and R2 are 1-2C-alkoxy.

A further special embodiment of the compounds of the present invention include those compounds of the formula I in which R1 and R2 are 1-2C-alkoxy and R3, R31 and R5 are hydrogen.

Another further special embodiment of the compounds of the present invention include those compounds of the formula I in which R4 is hydrogen.

Also another further special embodiment of the compounds of the present invention include those compounds of the formula I in which
R6 is 1-4C-alkoxy, completely or predominantly fluorine-substituted 1-4C-alkoxy, 3-7C-cycloalkylmethoxy, halogen, nitro, cyano, phenoxy, or C(O)OR61, wherein
R61 is hydrogen or 1-7C-alkyl, and
R7 is hydrogen, halogen, 1-4C-alkoxy, completely or predominantly fluorine-substituted 1-4C-alkoxy, or 3-7C-cycloalkylmethoxy.

A still further special embodiment of the compounds of the present invention include those compounds of the formula I in which
R1 is 1-2C-alkoxy, or completely or predominantly fluorine-substituted 1-2C-alkoxy,
R2 is 1-2C-alkoxy, or completely or predominantly fluorine-substituted 1-2C-alkoxy, and R3, R31 and R5 are hydrogen, whereby in this context compounds to be emphasized include those compounds of the formula I in which
R1 is ethoxy, and
R2 is methoxy or difluoromethoxy; or, in particular,
R1 is methoxy or difluoromethoxy, and
R2 is methoxy, difluoromethoxy or ethoxy; or, in more particular,
either
R1 is difluoromethoxy, and
R2 is methoxy or ethoxy, or
R1 is methoxy, and
R2 is ethoxy or difluoromethoxy;
and R3, R31 and R5 are hydrogen.

The compounds of the formula I are chiral compounds having chiral centers at least in positions 3, 4a and 10b and, depending on the meaning of the substituents R3, R31 and R5, further chiral centers in the positions 1, 2 and 4.

Numbering:

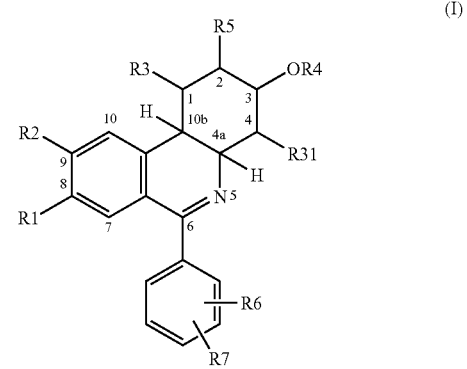

(I)

The invention therefore comprises all conceivable stereoisomers in pure form as well as in any mixing ratio.

Preferred compounds of the formula I are those in which the hydrogen atoms in positions 4a and 10b are in the cis position relative to one another. The pure cis diastereomers, the pure cis enantiomers and their mixtures in any mixing ratio and including the racemates are more preferred in this context. Particularly preferred in this connection are those compounds of the formula I which have, with respect to the positions 4a and 10b, the same configuration as shown in the formula I*:

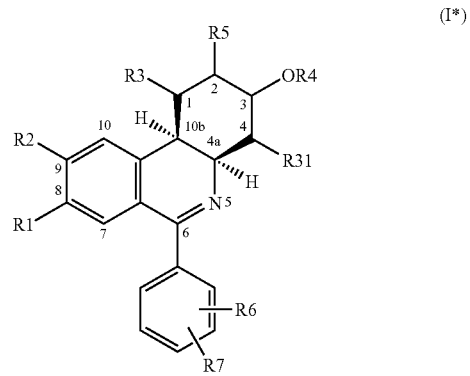

(I*)

If, for example in compounds of the formula I* R3, R31 and R5 have the meaning hydrogen, then the configuration— according the rules of Cahn, Ingold and Prelog—is R in the position 4a and R in the position 10b.

Further preferred compounds of the formula I are those which have, with respect to the positions 3, 4a and 10b, the same configuration as shown in the formulae I and I* and I****:

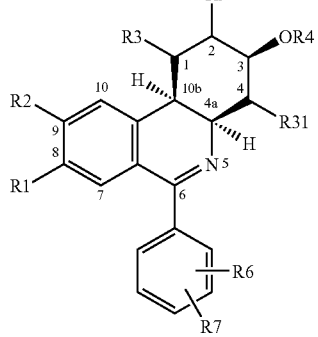
(I**)

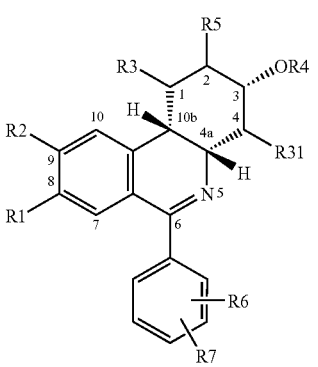
(I***)

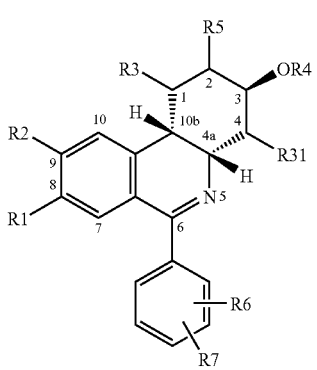
(I****)

If, for example in compounds of the formula I** R3, R31 and R5 have the meaning hydrogen, then the configuration—according the rules of Cahn, Ingold and Prelog—is R in the position 3, R in the position 4a and R in the position 10b.

If, for example in compounds of the formula I*** R3, R31 and R5 have the meaning hydrogen, then the configuration—according the rules of Cahn, Ingold and Prelog—is S in the position 3, S in the position 4a and S in the position 10b.

If, for example in compounds of the formula I**** R3, R31 and R5 have the meaning hydrogen, then the configuration—according the rules of Cahn, Ingold and Prelog—is R in the position 3, S in the position 4a and S in the position 10b.

Most preferred compounds of the formula I are those which have, with respect to the positions 3, 4a and 10b, the same configuration as shown in the formula I*****:

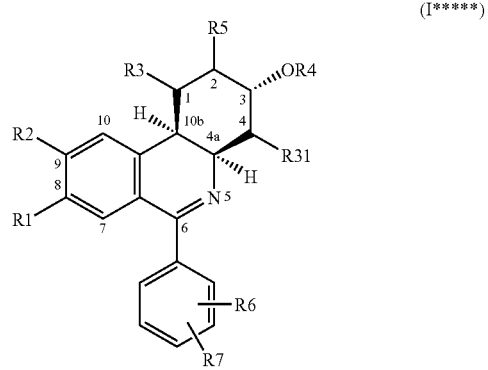
(I*****)

If, for example in compounds of the formula I***** R3, R31 and R5 have the meaning hydrogen, then the configuration—according the rules of Cahn, Ingold and Prelog—is S in the position 3, R in the position 4a and R in the position 10b.

As stated above all other possible stereoisomers of compounds of the formula I are also part of this invention.

The enantiomers can be separated in a manner known per se (for example by preparation and separation of appropriate diastereoisomeric compounds). For example, an enantiomer separation can be carried out at the stage of the starting compounds of the formulae VII in which R1, R2, R3, R31 and R5 have the meanings indicated above, or XVIa, in which R1, R2, R3, R31 and R5 have the meanings indicated above and PG represents a suitable protective group, for example acetyl. Further suitable protective groups are mentioned, for example, in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000). Alternatively, an enantiomer separation can be also carried out at the stage of the starting compounds of the formula XVIb, in which R1, R2, R3, R31, R4 and R5 have the abovementioned meanings.

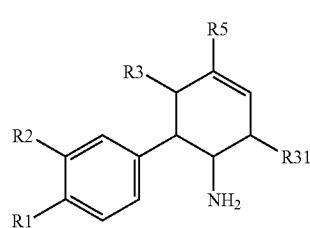
(VII)

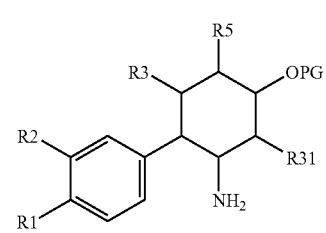
(XVIa)

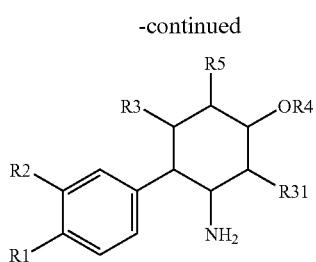

(XVIb)

Separation of the enantiomers can be carried out, for example, by means of salt formation of the racemic compounds of the formulae VII, XVIa or XVIb with optically active carboxylic acids, subsequent resolution of the salts and release of the desired compound from the salt. Examples of optically active carboxylic acids which may be mentioned in this connection are the enantiomeric forms of mandelic acid, tartaric acid, O,O'-dibenzoyltartaric acid, camphoric acid, quinic acid, glutamic acid, malic acid, camphorsulfonic acid, 3-bromocamphorsulfonic acid, α-methoxyphenylacetic acid, α-methoxy-α-trifluoromethylphenylacetic acid and 2-phenylpropionic acid. Alternatively, enantiomerically pure starting compounds of the formulae VII, XVIa or XVIb can be prepared via asymmetric syntheses. Enantiomerically pure starting compounds as well as enantiomerically pure compounds of the formula I can be also obtained by chromatographic separation on chiral separating columns; by derivatization with chiral auxiliary reagents, subsequent diastereomer separation and removal of the chiral auxiliary group; or by (fractional) crystallization from a suitable solvent.

The compounds according to the invention can be prepared, for example, according to the following reaction schemes.

In the first reaction step in reaction scheme 1 below, the nitro group of compounds of the formula VIII, in which R1, R2, R3, R31 and R5 have the meanings indicated above, is reduced to obtain corresponding compounds of the formula VII. Said reduction reaction is carried out in a manner known to the person skilled in the art, for example as described in J. Org. Chem. 1962, 27, 4426 or as described in the following examples. More specifically, the reduction can be carried out, for example, by contacting compounds of the formula VIII with a hydrogen-producing mixture such as, preferably, metallic zinc in a mildly acidic medium such as acetic acid in a lower alcohol such as methanol or ethanol at room temperature or at elevated temperature or, preferably, at the boiling temperature of the solvent mixture. Alternatively, the reduction can be carried out by selective reduction of the nitro group in a manner known to the person skilled in the art, for example by hydrogen transfer reaction in the presence of a metal catalyst, for example palladium or preferably Raney nickel, in a suitable solvent, preferably a lower alcohol, using, for example ammonium formiate or preferably hydrazine hydrate as hydrogen donor.

Reaction scheme 1:

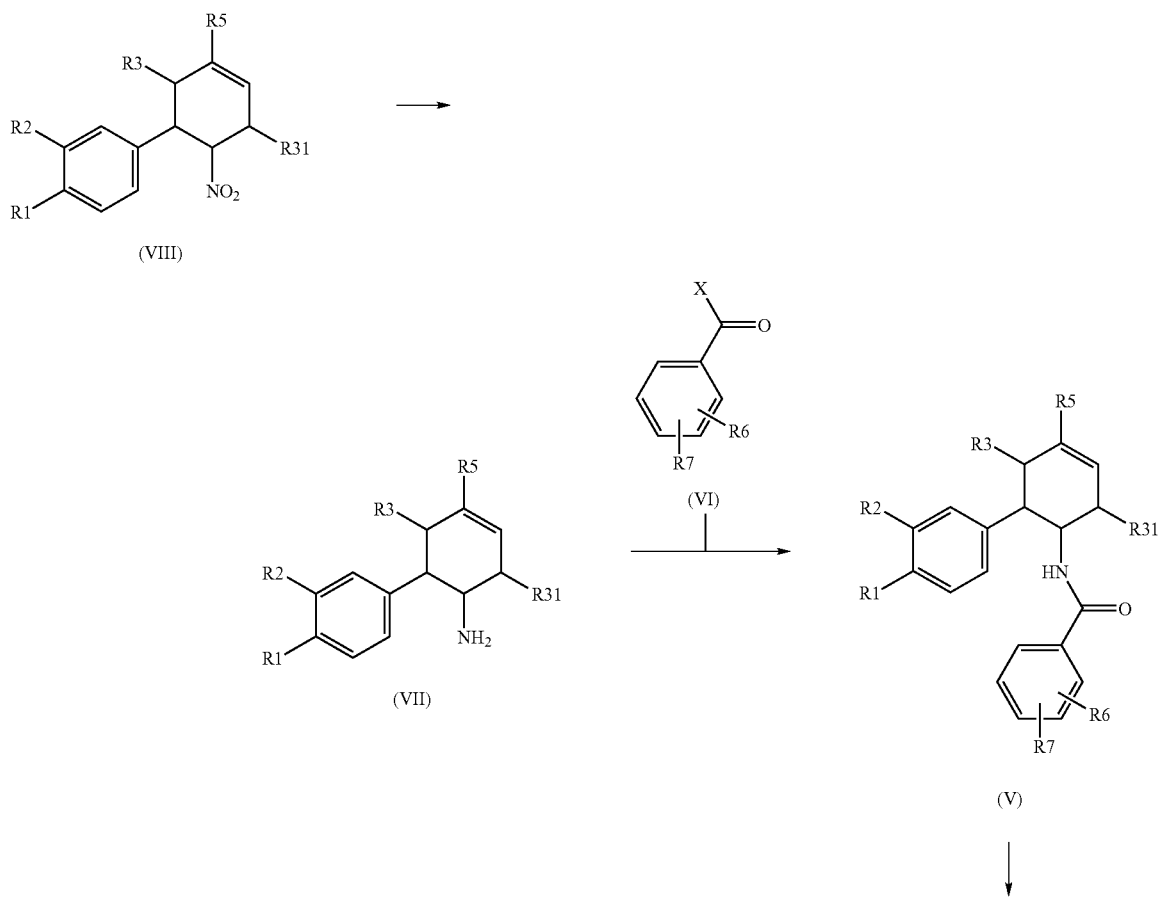

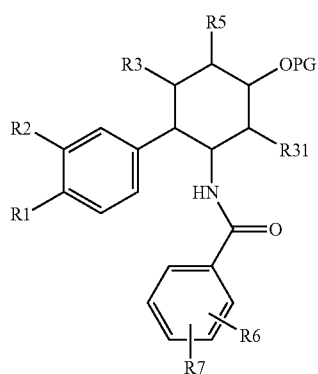 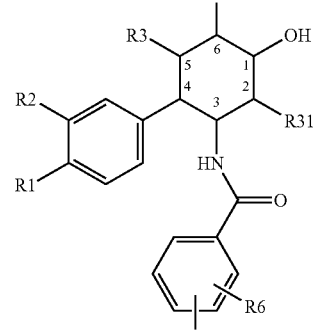 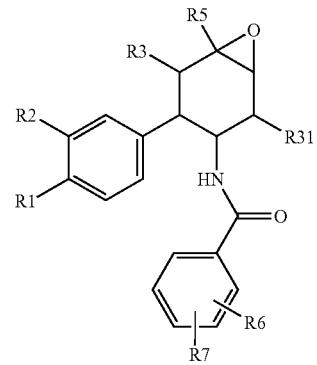

(IIa)　　　　　　　　(III)　　　　　　　　(IV)

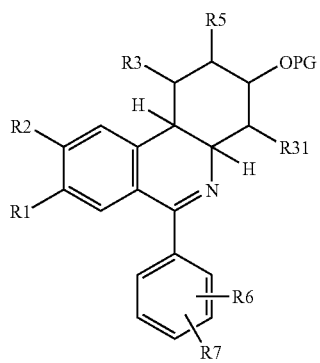 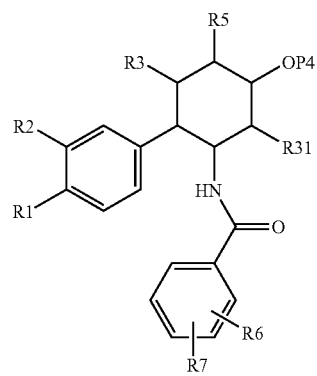

(Ia)　　　　　　　　(IIb)

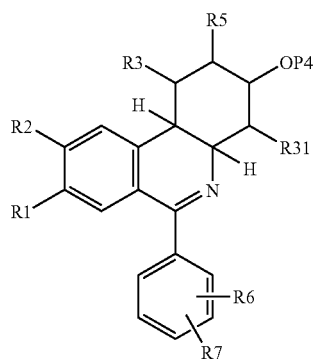

(I)

Compounds of the formula VII obtained can be reacted, for example, as described by way of example in the following examples with compounds of the formula VI, in which R6 and R7 have the meanings given above and X represents a suitable leaving group, preferably a chlorine atom, to give compounds of the formula V, in which R1, R2, R3, R31, R5, R6 and R7 have the abovementioned meanings.

Alternatively, compounds of the formula V, in which R1, R2, R3, R31, R5, R6 and R7 have the meanings given above, can also be prepared, for example, from compounds of the formula VII, in which R1, R2, R3, R31 and R5 have the meanings given above, and compounds of the formula VI, in which R6 and R7 have the said meanings and X is hydroxyl, by reaction with amide bond linking reagents known to the person skilled in the art. Exemplary amide bond linking reagents known to the person skilled in the art which may be mentioned are, for example, the carbodiimides (e.g. dicyclohexylcarbodiimide or, preferably, 1-ethyl-3-(3-dimethylaminopropyl)carbodiimide hydrochloride), azodicarboxylic acid derivatives (e.g. diethyl azodicarboxylate), uronium salts [e.g. O-(benzotriazol-1-yl)-N,N,N',N'-tetramethyluronium tetrafluoroborate or O-(benzotriazol-1-yl)-N,N,N',N'-tetramthyl-uronium-hexafluorophosphate] and N,N'-carbonyldiimidazole. In the scope of this invention preferred amide bond linking reagents are uronium salts and, particularly, carbodiimides, preferably, 1-ethyl-3-(3-dimethylaminopropyl)carbodiimide hydrochloride.

Compounds of the formula VI, wherein R6 and R7 have the abovementioned meanings, are either known or can be prepared in a known manner.

In the next step compounds of the formula V, in which R1, R2, R3, R31, R5, R6 and R7 have the said meanings, are converted into corresponding compounds of the formula IV by epoxidation reaction, which can be carried out as described in the following examples or in a manner known to one of ordinary skill in the art employing, for example, suitable epoxidation methods or suitable epoxidation reagents such as, for example, peracids (e.g. m-chloroperbenzoic acid) or organic or inorganic peroxides (e.g. dimethyldioxirane, hydrogene peroxide or persulfates).

Compounds of the formula IV obtained are reduced by art-known methods to corresponding compounds of the formula III. More specifically, said reduction reaction can be performed employing, for example, as described by way of example in the following examples sodium borohydride as reductant. Alternatively, said reduction reaction can be also carried out using, for example, lithium aluminium hydride or a reductive mixture comprising noble metals, such as platinium dioxide or palladium, and a suitable hydrogen donor. With the aid of each of those said reduction methods, compounds of the formula IV, in which R1, R2, R3, R31, R5, R6 and R7 have the abovementioned meanings, can be converted largely regio- and diastereoselectively into compounds of the formula III, wherein R1, R2, R3, R31, R5, R6 and R7 have the said meanings and the hydroxyl radical in position 1 and the amido radical in position 3 are located at the same side of the plane defined by the cyclohexane ring.

It is moreover known to one of ordinary skill of the art, that the absolute configuration of a chiral carbon atom, preferably, to which a hydroxyl group and a hydrogen atom are bonded, can be inverted. Thus the configuration of the carbon atom in position 1 of compounds of the formula III, wherein R1, R2, R3, R31, R5, R6 and R7 have the said meanings, can be optionally inverted. Said inversion of configuration of position 1 of compounds of the formula III can be achieved in a manner familiar to the person skilled in the art, for example by derivatization of position 1 with a suitable leaving group and subsequent replacement of said leaving group by a suitable nucleophile in a nucleophilic substitution reaction according to SN2 mechanism. Alternatively, said inversion of configuration of position 1 of compounds of the formula III can be also obtained, for example, as described by way of example in the following examples according to subsequently specified two step procedure shown in reaction scheme 2 below. In more detail, in the first step of said procedure shown in reaction scheme 2, exemplary compounds of the formula III*, in which R1, R2, R6 and R7 have the meanings indicated above and R3, R31, R5 are hydrogen and position 1 has the R configuration, are converted by oxidation reaction into corresponding compounds of the formula IX. Said oxidation is likewise carried out under conditions customary per se using, for example, chloranil, atmospheric oxygen, manganese dioxide or, preferably, chromium oxides as an oxidant. Then in the second step, compounds of the formula IX obtained are converted by art-known reduction reaction of the keto group, preferably with metal hydride compounds or, more specifically, metal borohydrides, such as, for example, sodium borohydride, into compounds of formula III**, in which R1, R2, R6 and R7 have the meanings indicated above and R3, R31, R5 are hydrogen and position 1 has now S configuration and thus the configuration of the carbon atom in position 1 is now inverted regarding to abovementioned compounds of the formula III*.

Reaction scheme 2:

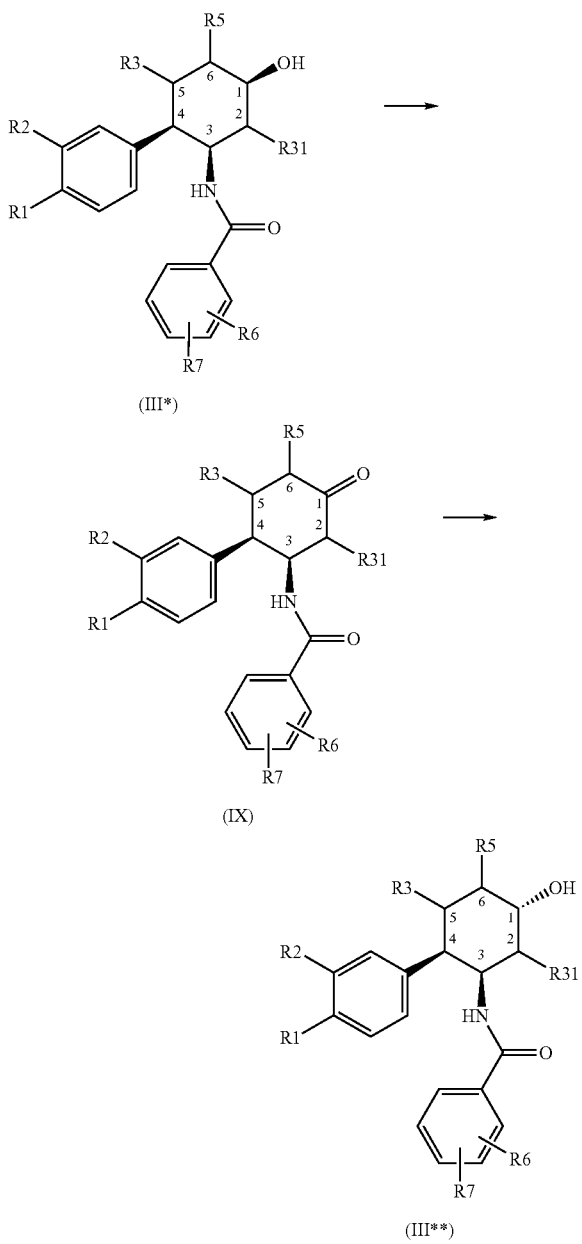

As shown in reaction scheme 1, compounds of the formula III, in which R1, R2, R3, R31, R5, R6 and R7 have the meanings given above, can be further processed by two different routes denoted as synthesis route A and synthesis route B.

Synthesis route A comprise the subsequently specified reaction steps: In the first reaction step of synthesis route A, the free hydroxyl group of compounds of the formula III, in which R1, R2, R3, R31, R5, R6 and R7 have the abovementioned meanings, is protected by a suitable protective group, for example acetyl or one of those mentioned, for example, in "Protective Groups in Organic Synthesis" by T. Greene and P. Wuts (John Wiley & Sons, Inc. 1999, $3^{rd}$ Ed.) or in "Protecting Groups (Thieme Foundations Organic Chemistry Series N Group" by P. Kocienski (Thieme Medical Publishers, 2000), to obtain compounds of the formula IIa, in which R1, R2, R3, R31, R5, R6 and R7 have the abovementioned meanings and PG represents said suitable protective group.

As shown in reaction scheme 1, compounds of the formula Ia, in which R1, R2, R3, R31, R5, R6 and R7 have the meanings indicated above and PG represents said suitable protective group, can be obtained according to synthesis route A by cyclocondensation of corresponding compounds of the formula IIa. Said cyclocondensation reaction is carried out in a manner known per se to the person skilled in the art or as described by way of example in the following examples, according to Bischler-Napieralski (e.g. as described in J. Chem. Soc., 1956, 4280-4282) in the presence of a suitable condensing agent, such as, for example, polyphosphoric acid, phosphorus pentachloride, phosphorus pentoxide or phosphorus oxychloride, in a suitable inert solvent, e.g. in a chlorinated hydrocarbon such as chloroform, or in a cyclic hydrocarbon such as toluene or xylene, or another inert solvent such as isopropyl acetate or acetonitrile, or without further solvent using an excess of condensing agent, at reduced temperature, or at room temperature, or at elevated temperature or at the boiling temperature of the solvent or condensing agent used.

Compounds of the formula I, in which R1, R2, R3, R31, R4, R5, R6 and R7 have the meanings given above, are accessible from compounds of the formula Ia, in which R1, R2, R3, R31, R5, R6 and R7 have the meanings indicated above and PG represents said suitable protective group, by reactions known to one of ordinary skill in the art or by reactions described in the following examples.

In more detail, for example, compounds of the formula I, in which R1, R2, R3, R31, R5, R6 and R7 have the meanings given above and R4 is hydrogen, can be obtained from compounds of the formula Ia, in which R1, R2, R3, R31, R5, R6 and R7 have the abovementioned meanings and PG represents said suitable protective group, by removal of the protective group in a manner described in the following examples or according to an art-known procedure mentioned, for example, in "Protective Groups in Organic Synthesis" by T. Greene and P. Wuts (John Wiley & Sons, Inc. 1999, $3^{rd}$ Ed.) or in "Protecting Groups (Thieme Foundations Organic Chemistry Series N Group" by P. Kocienski (Thieme Medical Publishers, 2000).

Optionally, said compounds of the formula I, in which R1, R2, R3, R31, R5, R6 and R7 have the meanings mentioned above and R4 is hydrogen, can be further derivatisized, preferably at the free hydroxyl group in position 3, by suitable reactions known to the person skilled in the art to obtain further compounds of the formula I.

In alternative to above specified synthesis route A, compounds of the formula III, in which R1, R2, R3, R31, R5, R6 and R7 have the meanings given above, can be also processed according to synthesis route B, which is also shown in reaction scheme 1.

In the first reaction step of said synthesis route B, compounds of the formula IIb, in which R1, R2, R3, R31, R4, R5, R6 and R7 have the meanings mentioned above, are prepared from compounds of the formula III, in which R1, R2, R3, R31, R5, R6 and R7 have the said meanings, by introduction of the group R4. The introduction reaction is carried out in a manner habitual per se or as described by way of example in the following examples.

The next reaction step of synthesis route B leading to compounds of the formula I, wherein R1, R2, R3, R31, R4, R5, R6 and R7 have the meanings given above, can be carried out, for example, as described by way of example in the following examples or according to an art-known manner or similarly as mentioned above for synthesis route A.

Optionally, compounds of formula I obtained either via synthesis route A or via synthesis route B can be converted into further compounds of the formula I by methods known to one of ordinary skill in the art. More specifically, for example, from compounds of the formula I in which a) R6 and/or R7 are an ester group, the corresponding acids can be obtained by acidic or alkaline hydrolysis;
b) R6 is a 1-4C-alkylcarbonyloxy group, the corresponding hydroxyl compounds can be obtained by acidic or alkaline hydrolysis;
c) R6 is a nitro group, the corresponding amino compounds, which, for their part, can again be further derivatized, can be obtained by selective reduction of the nitro group;
d) R4 is hydrogen, the corresponding ester compounds can be obtained by esterification reactions;
e) R4 is hydrogen, the corresponding ether compounds can be obtained by etherification reactions;
f) R4 is an acyl group, the corresponding hydroxyl compounds can be obtained by deesterification reactions;
g) R4 is an acyl group and R6 and/or R7 are an ester group, the corresponding compounds wherein R4 is hydrogen and R6 and/or R7 are carboxyl can be obtained by alkaline hydrolysis.

The methods mentioned under a), b), c), d), e), f) and g) are expediently carried out analogously to the methods known to the person skilled in the art or as described by way of example in the following examples.

Optionally, compounds of the formula I can be converted into their salts, or, optionally, salts of the compounds of the formula I can be converted into the free compounds.

In addition, the compounds of the formula I can be converted, optionally, into their N-oxides, for example with the aid of hydrogen peroxide in methanol or with the aid of m-chloroperoxybenzoic acid in dichloromethane. The person skilled in the art is familiar on the basis of his/her expert knowledge with the reaction conditions which are specifically necessary for carrying out the N-oxidation.

Compounds of the formula VIII, in which R1, R2, R3, R31 and R5 have the said meanings, are either known or can be obtained, for example as shown in reaction scheme 3, by the reaction of compounds of the formula XI, in which R1 and R2 have the abovementioned meanings, with compounds of the formula X, in which R3, R31 and R5 have the meanings indicated above.

Reaction scheme 3:

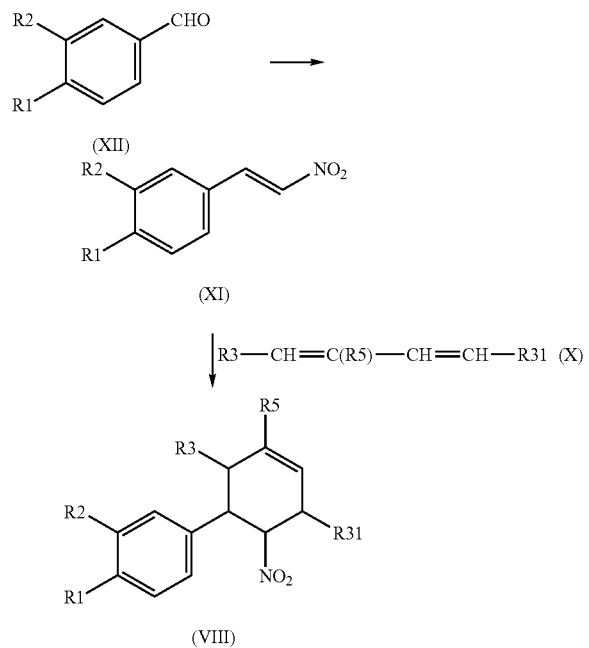

The cycloaddition is in this case carried out in a manner known to the person skilled in the art according to Diels-Alder, e.g. as described in J. Amer. Chem. Soc. 1957, 79, 6559 or in J. Org. Chem. 1952, 17, 581 or as described in the following examples.

Compounds of the formula VIII, in which the phenyl ring and the nitro group are trans to one another, can be converted such as known to the person skilled in the art into the corresponding cis compounds, e.g. as described in J. Amer. Chem. Soc. 1957, 79, 6559 or as described in the following examples.

The compounds of the formulae X and XI are either known or can be prepared in a known manner. The compounds of the formula XI can be prepared, for example, in a manner known to the person skilled in the art from compounds of the formula XIII as described, for example, in J. Chem. Soc. 1951, 2524 or in J. Org. Chem. 1944, 9, 170 or as described in the following examples.

The compounds of the formula XII, in which R1 and R2 have the meanings indicated above, are either known or can be prepared in a manner known to the person skilled in the art, as described, for example, in Ber. Dtsch. Chem. Ges. 1925, 58, 203.

Reaction scheme 4 below shows alternative synthesis routes for compounds of the formula IIa, in which R1, R2, R3, R31, R5, R6 and R7 have the meanings given above and PG represents said suitable protective group, and for compounds of the formula IIb, in which R1, R2, R3, R4, R31, R5, R6 and R7 have the meanings indicated above. The reactions within reaction scheme 3 can be carried out in a similar or analogous manner as specified above or in a manner known to the person skilled in the art.

Reaction scheme 4:

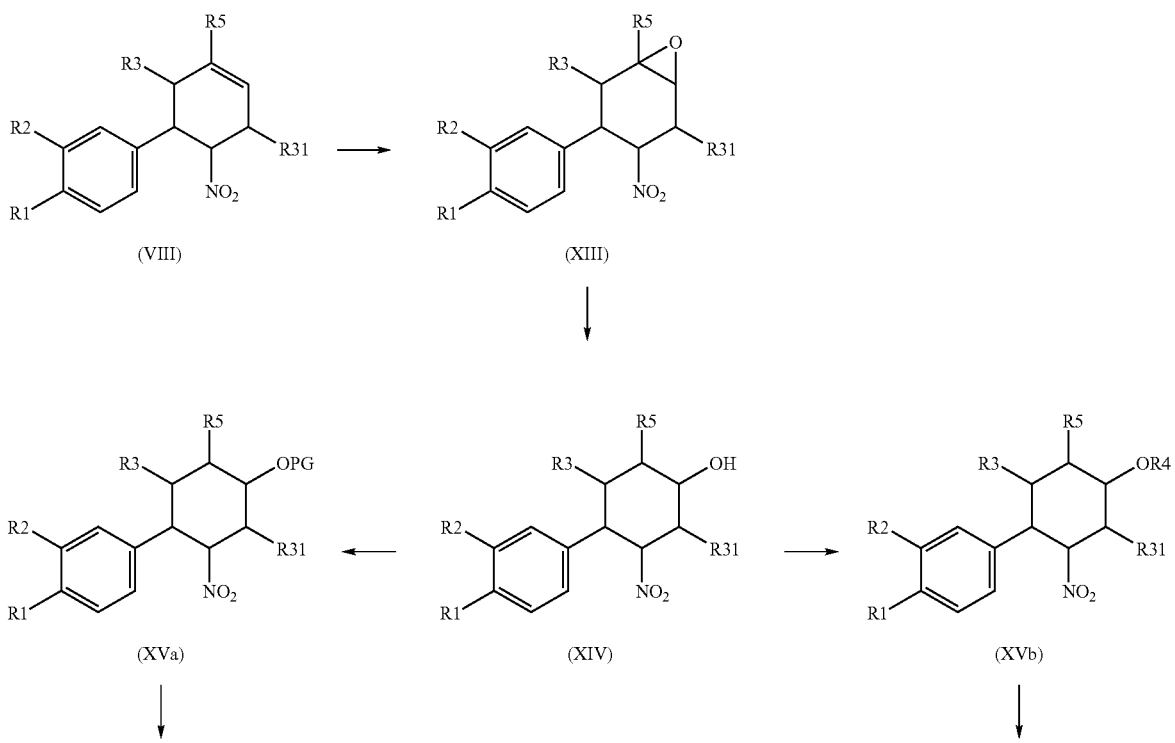

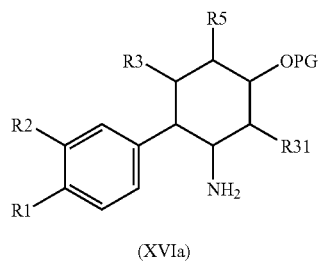

(XVIa)

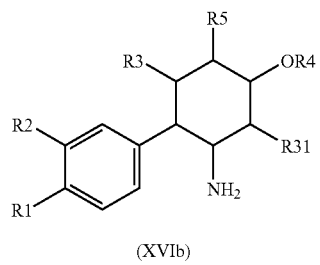

(XVIb)

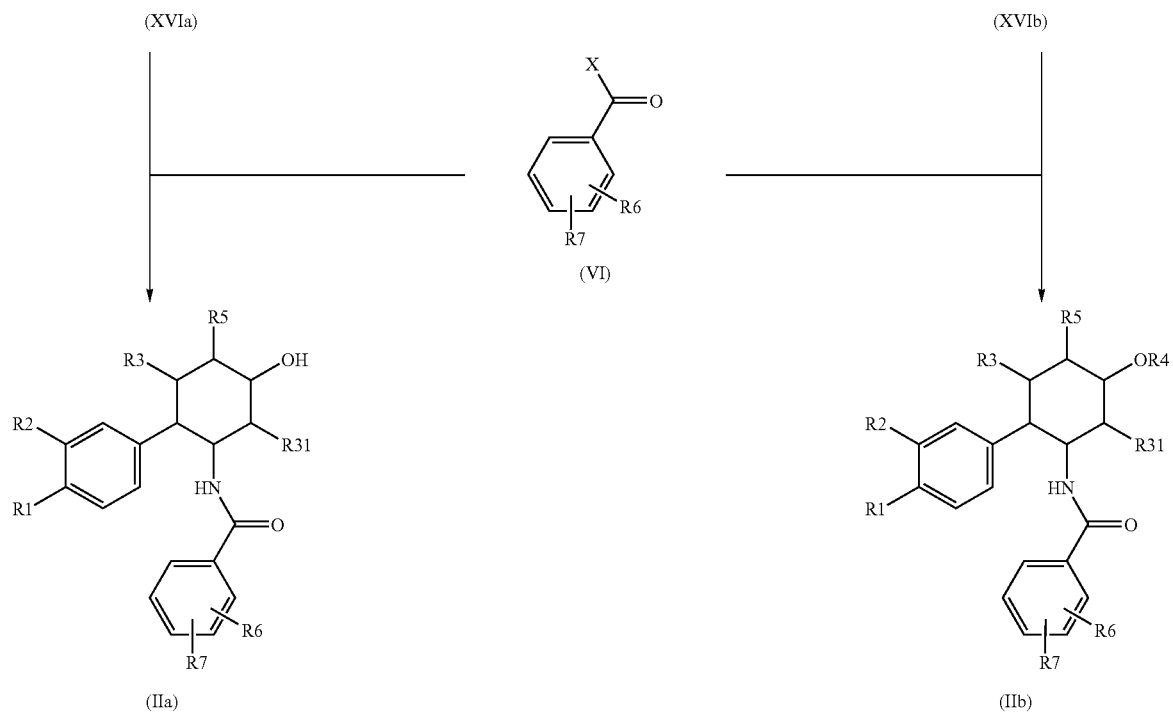

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, $3^{rd}$ Ed.) or in "Protecting Groups (Thieme Foundations Organic Chemistry Series N Group" by P. Kocienski (Thieme Medical Publishers, 2000).

The isolation and purification of the substances according to the invention is carried out in a manner known per se, e.g. by distilling off the solvent in vacuo and recrystallizing the resulting residue from a suitable solvent or subjecting it to one of the customary purification methods, such as, for example, column chromatography on suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low molecular weight aliphatic alcohol such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted by alkalization or by acidification into the free compounds, which in turn can be converted into salts. In this way, pharmacologically intolerable salts can be converted into pharmacologically tolerable salts.

The person skilled in the art knows on the basis of his/her knowledge and on the basis of those synthesis routes, which are shown and described within the description of this invention, how to find other possible synthesis routes for compounds of the formula I. All these other possible synthesis routes are also part of this invention.

Having described the invention in detail, the scope of the present invention is not limited only to those described characteristics or embodiments. As will be apparent to persons skilled in the art, modifications, analogies, variations and adaptations to the described invention can be made on the base of the disclosure (e.g. the explicite, implicite or inherent disclosure) of the present invention without departing from the spirit and scope of this invention.

The following examples serve to illustrate the invention in greater detail without restricting it. Likewise, further compounds of the formula I, whose preparation is not explicitly described, can also be prepared in an analogous manner or in a manner familiar per se to the person skilled in the art using customary process techniques.

In the examples, m.p. stands for melting point, h for hour(s), EF for empirical formula, MW for molecular weight, MS for mass spectrum, M for molecular ion.

According to common practice in stereochemistry, the symbols RS and SR are used to denote the specific configuration of each of the chiral centers of a racemate. In more detail, for example, the term "(3SR,4aRS,10bRS)" stands for a racemate comprising the one enantiomer having the configuration (3S,4aR,10bR) and the other enantiomer having the configuration (3R,4aS,10bS).

The compounds mentioned in the examples and their salts are a preferred subject of the invention.

EXAMPLES

Final Products 1. (±)-Acetic acid (3RS,4aRS,10bRS)-6-(3,4-bis-cyclopropylmethoxyphenyl)-8,9-dimethoxy-(1,2,3,4,4a,10b)-hexahydrophenanthridin-3-yl ester 3.0 g of phosphorus pentachloride are suspended in 18.6 ml of isopropyl acetate and 3.1 g of (±)-acetic acid (1RS,3RS,4RS)-3-{[1-(3,4-bis-cyclopropylmethoxyphenyl)methanoyl]-amino}-4-(3,4-dimethoxyphenyl)cyclohexyl ester (compound A1) are added portionwise. Afterwards, the reaction mixture is added under ice cooling to a mixture of 30 ml isopropyl acetate/triethylamine in the ratio 1/1. The mixture is diluted with 20 ml of water and washed with saturated sodium hydrogencarbonate solution, the organic phase is dried using sodium sulfate and concentrated. The residue is chromatographed on silica gel using a mixture of petroleum ether/ethyl acetate/triethylamine in the ratio 6/3/1 as eluent. After removal of the solvents of the appropriate eluate fractions, 2.3 g of the title compound are obtained as a foam.

EF: $C_{31}H_{37}NO_6$; MW: 519.64
MS: 520.3 (MH$^+$)

2. (±)-Acetic acid (3SR,4aRS,10bRS)-6(3,4-bis-cyclopropylmethoxyphenyl)-8,9-dimethoxy-(1,2,3,4,4a,10b)-hexahydrophenanthridin-3-yl ester 3.0 g of phosphorus pentachloride are suspended in 60 ml of isopropyl acetate and 2.7 g of (±)-acetic acid (1SR,3RS,4RS)-3-{[1-(3,4-bis-cyclopropylmethoxyphenyl)methanoyl]-amino}-4-(3,4-dimethoxyphenyl)cyclohexyl ester (compound A2) are added portionwise. Afterwards, the reaction mixture is added under ice cooling to a mixture of 60 ml isopropyl acetate/triethylamine in the ratio 1/1. The mixture is washed with water and saturated sodium hydrogencarbonate solution, the organic phase is dried using sodium sulfate and concentrated. The residue is purified by chromatography on silica gel using a mixture of petroleum ether/ethyl acetate/triethylamine in the ratio 6/3/1 as eluent. After removal of the solvents of the appropriate eluate fractions, 1.75 g of the title compound are obtained as colourless oil.

EF: $C_{31}H_{37}NO_6$; MW: 519.64
MS: 520.3 (MH$^+$)

3. (±)-(3RS,4aRS,10bRS)-6-(3,4-Bis-cyclopropyl-methoxyphenyl)-8,9-dimethoxy-(1,2,3,4,4a,10b)-hexahydrophenanthridin-3-ol 1.25 g of (±)-acetic acid (3RS,4aRS,10bRS)-6-(3,4-bis-cyclopropylmethoxyphenyl)-8,9-dimethoxy-(1,2,3,4,4a,10b)-hexahydrophenanthridin-3-yl ester (compound 1) are dissolved in 8.5 ml of ethanol, treated with 7 ml of a 1 M solution of potassium hydroxide and stirred at 45° C. for 1 h. The solution is concentrated, the residue is redissolved in ethyl acetate and extracted with water. The organic phase is dried using sodium sulfate and concentrated. The residue is chromatographed on silica gel using a mixture of petroleum ether/ethyl acetate/triethylamine in the ratio 6/3/1 as eluent. 770 mg of the title compound of m.p. 137-138° C. are obtained.

4. (±)-(3SR,4aRS,10bRS)-6-(3,4-Bis-cyclopropyl-methoxyphenyl)-8,9-dimethoxy-1,2,3,4,4a,10b-hexahydrophenanthridin-3-ol 1.65 g of (±)-acetic acid (3SR,4aRS,10bRS)-6-(3,4-bis-cyclopropylmethoxyphenyl)-8,9-dimethoxy-(1,2,3,4,4a,10b)-hexahydrophenanthridin-3-yl ester (compound 2) are dissolved in 60 ml of abs. ethanol, treated with 15 ml of a 1 M solution of potassium hydroxide in ethanol and stirred for 0.5 h at room temperature. The solution is concentrated, the residue redissolved in ethyl acetate, extracted with water, dried using sodium sulfate and concentrated. 1.1 g of the title compound of m.p. 172.5-174° C. are obtained.

5. (±)-Acetic acid (3SR,4aRS,10bRS)-6-(4-cy-anophenyl)-8,9-dimethoxy-(1,2,3,4,4a,10b)-hexahy-drophenanthridin-3-yl ester Starting from the appropriate starting compound mentioned below, the title compound can be obtained analogously to the procedure as in Example 2.

EF: $C_{24}H_{24}N_2O_4$; MW: 404.47
MS: 405.2 (MH$^+$)

6. (±)-4-((3SR,4aRS,10bRS)-3-Hydroxy-8,9-dimethoxy-(1,2,3,4,4a,10b)-hexahydrophenanthri-din-6-yl)-benzonitrile Starting from (±)-acetic acid (3SR,4aRS,10bRS)-6-(4-cy-anophenyl)-8,9-dimethoxy-(1,2,3,4,4a,10b)-hexahydro-phenanthridin-3-yl ester (compound 5), the title compound can be obtained analogously to the procedure as in Example 4.

EF: $C_{22}H_{22}N_2O_3$; MW: 362.43
MS: 363.3 (MH$^+$)

Starting Compounds:

A1. (±)-Acetic acid (1RS,3RS,4RS)-3-{[1-(3,4-bis-cyclopropylmethoxyphenyl)methanoyl]-amino}-4-(3,4-dimethoxyphenyl)cyclohexyl ester 3.2 g of (±)-3,4-bis-cyclopropylmethoxy-N-[(1RS,2RS,5RS)-2-(3,4-dimethoxyphenyl)-5-hydroxycyclohexyl]ben-zamide (compound D1) are dissolved in 70 ml of acetic anhydride and the solution is heated to 100° C. for 5 h. The solution is concentrated and the residue is recrystallized in ethanol. 3.15 g of the title compound of m.p. 148-151° C. are obtained.

A2. (±)-Acetic acid (1SR,3RS,4RS)-3-{[1-(3,4-bis-cyclopropylmethoxyphenyl)methanoyl]amino}-4-(3,4-dimethoxyphenyl)cyclohexyl ester 3.65 g of (±)-3,4-bis-cyclopropylmethoxy-N-[(1RS,2RS,5SR)-2-(3,4-dimethoxyphenyl)-5-hydroxycyclohexyl]ben-zamide (compound B2) are dissolved in 50 ml of acetic anhy-dride and the solution is heated to 100° C. for 3 h. The solution is concentrated and the residue is chromatographed on silica gel using a mixture of petroleum ether/ethyl acetate/triethylamine in the ratio 6/3/1. 1.8 g of the title compound of m.p. 90-95° C. are obtained.

A3. (±)-Acetic acid (1SR,3RS,4RS)-3-{[1-(4-cyanophenyl)methanoyl]amino}-4-(3,4-dimethoxyphenyl) cyclohexyl ester Starting from the appropriate starting compound, which can be prepared in a manner known to the person skilled in the art or analogously or similarly to the Examples described herein, the title compound can be obtained analogously to Example A2.
EF: $C_{24}H_{26}N_2O_5$; MW: 422.49
MS: 423.0 (MH$^+$)

B1. (±)-3,4-Bis-cyclopropylmethoxy-N-[(1RS,2RS,5SR)-2-(3,4-dimethoxyphenyl)-5-hydroxycyclohexyl]benzamide 7.2 g of (±)-3,4-bis-cyclopropylmethoxy-N-[(1RS,2RS)-2-(3,4-dimethoxyphenyl)-5-oxo-cyclohexyl]benzamide (compound C1) are dissolved in 550 ml of 1,2-dimethoxyethane and 34 ml of methanol and treated portionwise with 600 mg of sodium borohydride at room temperature. The reaction mixture is concentrated, the residue redissolved in ethyl acetate and extracted with water. The organic layer is dried using sodium sulfate, concentrated and the residue is chromatographed on silica gel using a mixture of petroleum ether/ethyl acetate/triethylamine in the ratio 6/3/1. 6.35 g of the title compound are obtained.

C1. (±)-3,4-Bis-cyclopropylmethoxy-N-[(1RS,2RS)-2-(3,4-dimethoxyphenyl)-5-oxo-cyclohexyl]-benzamide A solution of 8.0 g of (±)-3,4-bis-cyclopropylmethoxy-N-[(1RS,2RS,5RS)-2-(3,4-dimethoxyphenyl)-5-hydroxycyclohexyl]benzamide (compound D1) in 80 ml of dichloromethane is added dropwise to a suspension of 10 g of chromium (III) oxide in 160 ml of dichloromethane and 16 ml of pyridine. After stirring for 2 h at room temperature, the reaction mixture is extracted with 6 N sodium hydroxide solution, 2 N hydrochloric acid and finally water. The organic phase is dried using sodium sulfate and concentrated. 7.3 g of the title compound of m.p. 150-151.5° C. are obtained.

D1. (±)-3,4-Bis-cyclopropylmethoxy-N-[(1RS,2RS,5RS)-2-(3,4-dimethoxyphenyl)-5-hydroxycyclohexyl]benzamide 16.5 g of (±)-3,4-bis-cyclopropylmethoxy-N-[(3RS,4RS)-4-(3,4-dimethoxyphenyl)-7-oxabicyclo[4.1.0]-hept-3-yl] benzamide (compound E1) are dissolved in 500 ml of tert-butanol, 5.0 g of sodium borohydride are added and the reaction mixture is heated to boiling. After slow addition of 70 ml of methanol, the reaction mixture is cooled and treated with 200 ml of water and 150 ml of ethyl acetate. The organic phase is dried using sodium sulfate, concentrated and the residue is chromatographed on silica gel using a mixture of petroleum ether/ethyl acetate in the ratio 1/2. 11.3 g of the title compound are obtained.

E1. (±)-3,4-Bis-cyclopropylmethoxy-N-[(3RS,4RS)-4-(3,4-dimethoxyphenyl)-7-oxabicyclo[4.1.0]-hept-3-yl]benzamide 37.7 g of (±)-cis-3,4-bis-cyclopropylmethoxy-N-[6-(3,4-dimethoxyphenyl)cyclohex-3-enyl]benzamide (compound F1) are dissolved in 470 ml of dichloromethane and treated with 27.4 g of m-chloroperbenzoic acid. After stirring over night at room temperature, the reaction mixture is extracted with sodium hydrogencarbonate solution and water, the organic phase is dried using sodium sulfate and concentrated. The residue is chromatographed on silica gel using a a mixture of petroleum ether/ethyl acetate/triethylamine in the ratio 4/4/1. 26.5 g of the title compound are obtained.

F1. (±)-cis-3,4-Bis-cyclopropylmethoxy-N-[6-(3,4-dimethoxyphenyl)cyclohex-3-enyl]benzamide 20 g of (±)-cis-6-(3,4-dimethoxyphenyl)-cyclohex-3-enylamine (compound G1) are dissolved in 125 ml of dichloromethane and treated with a solution of 24.1 g of 3,4-bis-cyclopropylmethoxybenzoyl chloride in 125 ml of dichloromethane at room temperature. After 1 h the reaction mixture is extracted with 2 N hydrochloric acid and water, the organic phase is dried using sodium sulfate and concentrated. 38.3 g of the title compound of m.p. 152-153.5° C. are obtained.

G1. (±)-cis-6-(3,4-Dimethoxyphenyl)-cyclohex-3-enylamine 40 g of (±)-cis-1,2-dimethoxy-4-(2-nitrocyclohex-4-enyl) benzene (compound H1) are dissolved in 400 ml of ethanol and 40 g of zinc powder are added. After heating to boiling temperature, 65 ml of glacial acetic acid are added dropwise. Afterwards, the reaction mixture is filtrated and concentrated. The residue is redissolved in diluted hydrochloric acid and extraxted with toluene. The aqueous layer is alkalized using 6 N solution of sodium hydroxide and extracted several times with toluene. The combined organic phases of the alkalic extraction are dried using sodium sulfate and concentrated. The residue is chromatographed on silica gel using a mixture of petroleum ether/ethyl acetate/triethylamine in the ratio 6/3/1. 11.5 g of the title compound are obtained.

H1. (±)-cis-1,2-Dimethoxy-4-(2-nitrocyclohex-4-enyl)benzene 10.0 g of (±)-trans-1,2-dimethoxy-4-(2-nitrocyclohex-4-enyl)benzene (compound I1) and 20.0 g of potassium hydroxide are dissolved in 150 ml of ethanol and 35 ml of dimethylformamide. A solution of 17.5 ml of conc. sulfuric acid in 60 ml of ethanol is then added dropwise such that the internal temperature does not exceed 4° C. After stirring for 1 h, the mixture is added to 1 l of ice water, the precipitate is filtered off with suction, washed with water and dried, and the crude product is recrystallized in ethanol. 8.6 g of the title compound of m.p. 82.5-84° C. are obtained.

I1. (±)-trans-1,2-Dimethoxy-4-(2-nitrocyclohex-4-enyl)benzene 50.0 g of 3,4-dimethoxy-nitrostyrene (compound J1), and 1.0 g (9.1 mmol) of hydroquinone are suspened in 200 ml of abs. toluene and treated at −70° C. with 55.0 g (1.02 mol) of liquid 1,3-butadiene. The mixture is stirred at 160° C. for 6 days in an autoclave and then cooled. Some of the solvent is removed on a rotary evaporator, and the resulting precipitate is filtered off with suction and recrystallized in ethanol. M.p.: 113.5-115.5° C.

J1. 3,4-Dimethoxy-ω-nitrostyrene 207.0 g of 3,4-dimethoxybenzaldehyde, 100.0 g of ammonium acetate and 125 ml of nitromethane are heated to boiling for 3-4 h in 1.0 l of glacial acetic acid. After cooling in an ice bath, the precipitate is filtered off with suction, rinsed with glacial acetic acid and petroleum ether and dried. M.p.: 140-141° C. Yield: 179.0 g.

COMMERCIAL UTILITY

The compounds according to the invention have useful pharmacological properties which make them industrially utilizable. As selective cyclic nucleotide phosphodiesterase (PDE) inhibitors (specifically of type 4), they are suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways (asthma prophylaxis), of the skin, of the intestine, of the eyes, of the CNS and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. In this context, the compounds according to the invention are distinguished by a low toxicity, a good enteral absorption (high bioavailability), a large therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of varying origin (bronchitis, allergic bronchitis, bronchial asthma, emphysema, COPD); dermatoses (especially of proliferative, inflammatory and allergic type) such as psoriasis (vulgaris), toxic and allergic contact eczema, atopic eczema, seborrhoeic eczema, Lichen simplex, sunburn, pruritus in the anogenital area, alopecia greata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, for example disorders of the arthritis type (rheumatoid arthritis, rheumatoid spondylitis, osteoarthritis and other arthritic conditions), disorders of the immune system (AIDS, multiple sclerosis), graft versus host reaction, allograft rejections, types of shock (septic shock, endotoxin shock, gram-negative sepsis, toxic shock syndrome and ARDS (adult respiratory distress syndrome)) and also generalized inflammations in the gastrointestinal region (Crohn's disease and ulcerative colitis); disorders which are based on allergic and/or chronic, immunological false reactions in the region of the upper airways (pharynx, nose) and the adjacent regions (paranasal sinuses, eyes), such as allergic rhinitis/sinusitis, chronic rhinitis/sinusitis, allergic conjunctivitis and also nasal polyps; but also disorders of the heart which can be treated by PDE inhibitors, such as cardiac insufficiency, or disorders which can be treated on account of the tissue-relaxant action of the PDE inhibitors, such as, for example, erectile dysfunction or colics of the kidneys and of the ureters in connection with kidney stones. In addition, the compounds of the invention are useful in the treatment of diabetes insipidus and conditions associated with cerebral metabolic inhibition, such as cerebral senility, senile dementia (Alzheimer's disease), memory impairment associated with Parkinson's disease or multiinfarct dementia; and also illnesses of the central nervous system, such as depressions or arteriosclerotic dementia.

The invention further relates to a method for the treatment of mammals, including humans, which are suffering from one of the above mentioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of pharmaceutical compositions which are employed for the treatment and/or prophylaxis of the illnesses mentioned.

The invention also relates to the use of the compounds according to the invention for the production of pharmaceutical compositions for treating disorders which are mediated by phosphodiesterases, in particular PDE4-mediated disorders, such as, for example, those mentioned in the specification of this invention or those which are apparent or known to the skilled person.

The invention furthermore relates to pharmaceutical compositions for the treatment and/or prophylaxis of the illnesses mentioned, which contain one or more of the compounds according to the invention.

Additionally, the invention relates to an article of manufacture, which comprises packaging material and a pharmaceutical agent contained within said packaging material, wherein the pharmaceutical agent is therapeutically effective for antagonizing the effects of the cyclic nucleotide phosphodiesterase of type 4 (PDE4), ameliorating the symptoms of an PDE4-mediated disorder, and wherein the packaging material comprises a label or package insert which indicates that the pharmaceutical agent is useful for preventing or treating PDE4-mediated disorders, and wherein said pharmaceutical agent comprises one or more compounds of formula 1 according to the invention. The packaging material, label and package insert otherwise parallel or resemble what is generally regarded as standard packaging material, labels and package inserts for pharmaceuticals having related utilities.

The pharmaceutical compositions are prepared by processes which are known per se and familiar to the person skilled in the art. As pharmaceutical compositions, the compounds according to the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral delivery is preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 µm, advantageously of 2 to 6 µm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those pharmaceutical compositions which are suitable for topical application. For the production of the pharmaceutical compositions, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for PDE inhibitors. Topical application forms (such as ointments) for the treatment of dermatoses thus contain the active compounds in a concentration of, for example, 0.1-99%. The dose for administration by inhalation is customarily between 0.01 and 3 mg per day. The customary dose in the case of systemic therapy (p.o. or i.v.) is between 0.003 and 3 mg/kg per day. In another embodiment, the dose for administration by inhalation is between 0.1 and 3 mg per day, and the dose in the case of systemic therapy (p.o. or i.v.) is between 0.03 and 3 mg/kg per day.

Biological Investigations

The second messenger cyclic AMP (cAMP) is well-known for inhibiting inflammatory and immunocompetent cells. The PDE4 isoenzyme is broadly expressed in cells involved in the initiation and propagation of inflammatory diseases (H Tenor and C Schudt, in "Phosphodiesterase Inhibitors", 21-40, "The Handbook of Immunopharmacology", Academic Press, 1996), and its inhibition leads to an increase of the intracellular cAMP concentration and thus to the inhibition of cellular activation (J E Souness et al., Immunopharmacology 47: 127-162, 2000).

The antiinflammatory potential of PDE4 inhibitors in vivo in various animal models has been described (M M Teixeira, TiPS 18: 164-170,1997). For the investigation of PDE4 inhibition on the cellular level (in vitro), a large variety of proinflammatory responses can be measured. Examples are the superoxide production of neutrophilic (C Schudt et al., Arch Pharmacol 344: 682-690, 1991) or eosinophilic (A Hatzelmann et al., Brit J Pharmacol 114: 821-831, 1995) granulocytes, which can be measured as luminol-enhanced chemiluminescence, or the synthesis of tumor necrosis factor-α in monocytes, macrophages or dendritic cells (Gantner et al., Brit J Pharmacol 121: 221-231, 1997, and Pulmonary Pharmacol Therap 12: 377-386,1999). In addition, the immunomodulatory potential of PDE4 inhibitors is evident from the inhibition of T-cell responses like cytokine synthesis or proliferation (D M Essayan, Biochem Pharmacol 57: 965-973, 1999). Substances which inhibit the secretion of the aforementioned proinflammatory mediators are those which inhibit PDE4. PDE4 inhibition by the compounds according to the invention is thus a central indicator for the suppression of inflammatory processes.

Methods for Measuring Inhibition of PDE4 Activity

Method a:

PDE4 activity was determined as described by Thompson et al. (Adv Cycl Nucl Res 10: 69-92, 1979) with some modifications (Bauer and Schwabe, Naunyn-Schmiedeberg's Arch Pharmacol 311: 193-198, 1980). At a final assay volume of 200 µl (96 well microtiter plates) the assay mixture contained 20 mM Tris (pH 7.4), 5 mM $MgCl_2$, 0.5 µM cAMP, [$^3$H]cAMP (about 30,000 cpm/assay), the test compound and an aliquot of cytosol from human neutrophils which mainly contains PDE4 activity as described by Schudt et al. (Naunyn-Schmiedeberg's Arch Pharmacol 344: 682-690, 1991); the PDE3-specific inhibitor Motapizone (1 µM) was included to suppress PDE3 activity originating from contaminating platelets. Serial dilutions of the compounds were prepared in DMSO and further diluted 1:100 (v/v) in the assays to obtain the desired final concentrations of the inhibitors at a DMSO concentration of 1% (v/v) which by itself only slightly affected PDE4 activity.

After preincubation for 5 min at 37° C., the reaction was started by the addition of substrate (CAMP) and the assays were incubated for further 15 min at 37° C. 50 µl of 0.2 N HCl was added to stop the reaction and the assays were left on ice for about 10 min. Following incubation with 25 µg 5'-nucleotidase (Crotalus atrox snake venom) for 10 min at 37° C., the assays were loaded on QAE Sephadex A-25 (1 ml bed volume). The columns were eluted with 2 ml of 30 mM ammonium formiate (pH 6.0) and the eluate was counted for radioactivity. Results were corrected for blank values (measured in the presence of denatured protein) which were below 5% of total radioactivity. The amount of cyclic nucleotides hydrolyzed did not exceed 30% of the original substrate concentration. The $IC_{50}$-values for the compounds according to the invention for the inhibition of the PDE4 activity were determined from the concentration-inhibition curves by nonlinear-regression.

Method b:

The PDE4B2 (GB no. M97515) was a gift of Prof. M. Conti (Stanford University, USA). It was amplified from the original plasmid (pCMV5) via PCR with primers Rb9 (5'-GC-CAGCGTGCAAATAATGAAGG-3') and Rb10 (5'-AGAGGGGGATTATGTATCCAC-3') and cloned into the pCR-Bac vector (Invitrogen, Groningen, NL).

The recombinant baculovirus was prepared by means of homologous recombination in SF9 insect cells. The expression plasmid was cotransfected with Bac-N-Blue (Invitrogen, Groningen, NL) or Baculo-Gold DNA (Pharmingen, Hamburg) using a standard protocol (Pharmingen, Hamburg). Wt virus-free recombinant virus supernatant was selected using plaque assay methods. After that, high-titre virus supernatant was prepared by amplifying 3 times. PDE was expressed in SF21 cells by infecting $2\times10^6$ cells/ml with an MOI (multiplicity of infection) between 1 and 10 in serum-free SF900 medium (Life Technologies, Paisley, UK). The cells were cultured at 28° C. for 48-72 hours, after which they were pelleted for 5-10 min at 1000 g and 4° C.

The SF21 insect cells were resuspended, at a concentration of approx. $10^7$ cells/ml, in ice-cold (4° C.) homogenization buffer (20 mM Tris, pH 8.2, containing the following additions: 140 mM NaCl, 3.8 mM KCl, 1 mM EGTA, 1 mM $MgCl_2$, 10 mM β-mercaptoethanol, 2 mM benzamidine, 0.4 mM Pefablock, 10 μM leupeptin, 10 μM pepstatin A, 5 μM trypsin inhibitor) and disrupted by ultrasonication. The homogenate was then centrifuged for 10 min at 1000×g and the supernatant was stored at −80° C. until subsequent use (see below). The protein content was determined by the Bradford method (BioRad, Munich) using BSA as the standard.

PDE4B2 activity is inhibited by the said compounds in a modified SPA (scintillation proximity assay) test, supplied by Amersham Biosciences (see procedural instructions "phosphodiesterase [3H]cAMP SPA enzyme assay, code TRKQ 7090"), carried out in 96-well microtitre plates (MTP's). The test volume is 100 μl and contains 20 mM Tris buffer (pH 7.4), 0.1 mg of BSA (bovine serum albumin)/ml, 5 mM $Mg^{2+}$, 0.5 μM cAMP (including about 50,000 cpm of [3H]cAMP), 1 μl of the respective substance dilution in DMSO and sufficient recombinant PDE (1000×g supernatant, see above) to ensure that 10-20% of the cAMP is converted under the said experimental conditions. The final concentration of DMSO in the assay (1% v/v) does not substantially affect the activity of the PDE investigated. After a preincubation of 5 min at 37° C., the reaction is started by adding the substrate (cAMP) and the assay is incubated for a further 15 min; after that, it is stopped by adding SPA beads (50 μl). In accordance with the manufacturer's instructions, the SPA beads had previously been resuspended in water, but were then diluted 1:3 (v/v) in water; the diluted solution also contains 3 mM IBMX to ensure a complete PDE activity stop. After the beads have been sedimented (>30 min), the MTP's are analyzed in commercially available luminescence detection devices. The corresponding $IC_{50}$ values of the compounds for the inhibition of PDE activity are determined from the concentration-effect curves by means of non-linear regression.

The inhibitory values determined for the compounds according to the invention follow from the following table A, in which the numbers of the compounds correspond to the numbers of the examples.

The inhibitory values of the compounds 3 and 4 have been determined according to Method a.

TABLE A

Inhibition of the PDE4 activity

| Compound | −log $IC_{50}$ |
|---|---|
| 3 | 6.84 |
| 4 | 8.53 |

The invention claimed is:
1. A compound of the formula I

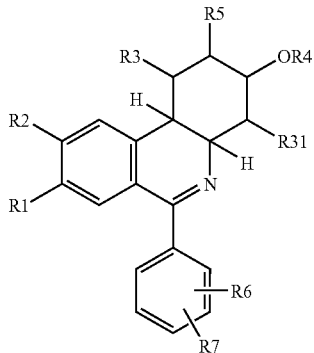

(I)

in which
R1 is methoxy or difluoromethoxy,
R2 is methoxy difluoromethoxy or ethoxy,
R3 is hydrogen,
R31 is hydrogen,
R4 is hydrogen or acetyl,
R5 hydrogen,
R6 is cyano or cyclopropylmethoxy,
R7 is hydrogen or cyclopropylmethoxy, or a salt of this compound, an N-oxide of this compound, or a salt of an N-oxide of this compound.

2. A compound of the formula I as claimed in claim 1, in which
R1 is methoxy,
R2 is methoxy,
R3 is hydrogen,
R31 is hydrogen,
R4 is hydrogen or acetyl,
R5 is hydrogen,
R6 is cyano or cyclopropylmethoxy,
R7 is hydrogen or cyclopropylmethoxy, or a salt of this compound, an N-oxide of this compound, or a salt of an N-oxide of this compound.

3. A compound of the formula I as claimed in claim 1, in which
R1 is methoxy,
R2 is methoxy,
R3 is hydrogen,
R31 is hydrogen,
R4 is hydrogen or acetyl,
R5 is hydrogen,
R6 is cyclopropylmethoxy,
R7 is cyclopropylmethoxy, or a salt of this compound, an N-oxide of this compound, or a salt of an N-oxide of this compound.

4. A compound as claimed in claim 1, selected from the group consisting of
(±)-acetic acid (3RS,4aRS,10bRS)-6-(3,4-bis-cyclopropylmethoxyphenyl)-8,9-dimethoxy-(1,2,3,4,4a,10b)-hexahydrophenanthridin-3-yl ester,
(±)-acetic acid (3SR,4aRS,10bRS)-6-(3,4-bis-cyclopropylmethoxyphenyl)-8,9-dimethoxy-(1,2,3,4,4a,10b)-hexahydrophenanthridin-3-yl ester,
(±)-(3RS,4aRS,10bRS)-6-(3,4-bis-cyclopropylmethoxyphenyl)-8,9-dimethoxy-(1,2,3,4,4a,10b)-hexahydrophenanthridin-3-ol,
(±)-(3SR,4aRS,10bRS)-6-(3,4-bis-cyclopropylmethoxyphenyl)-8,9-dimethoxy-1,2,3,4,4a,10b-hexahydrophenanthridin-3-ol,
(±)-acetic acid (3SR,4aRS,10bRS)-6-(4-cyanophenyl)-8,9-dimethoxy-(1,2,3,4,4a,10b)-hexahydrophenanthridin-3-yl ester,
(±)-4-((3SR,4aRS,10bRS)-3-hydroxy-8,9-dimethoxy-(1,2,3,4,4a,10b)-hexahydrophenanthridin-6-yl)-benzonitrile, and the salts of these compounds, the N-oxides of these compounds, and the salts of the N-oxides of these compounds.

5. A compound of the formula I according to claim 1, in which the hydrogen atoms in positions 4a and 10b are in the cis position relative to one another, or a salt of this compound, an N-oxide of this compound, or a salt of an N-oxide of this compound.

6. A compound of the formula I according to claim 1, which has with respect to the positions 4a and 10b, the configuration shown in the formula I*:

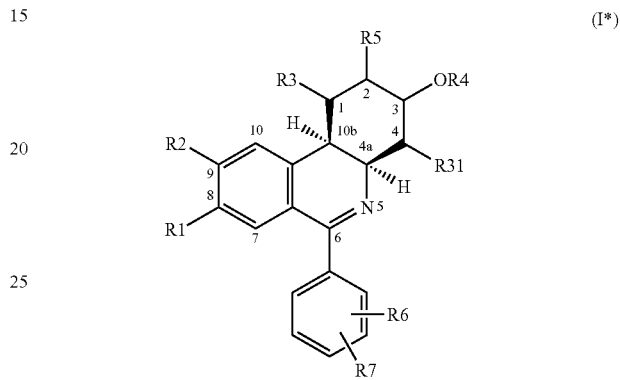

(I*)

or a salt of this compound, an N-oxide of this compound, or a salt of an N-oxide of this compound.

7. A compound of the formula I according to claim 1, which has with respect to the positions 3, 4a and 10b, the configuration shown either in formula I, I* or I****:

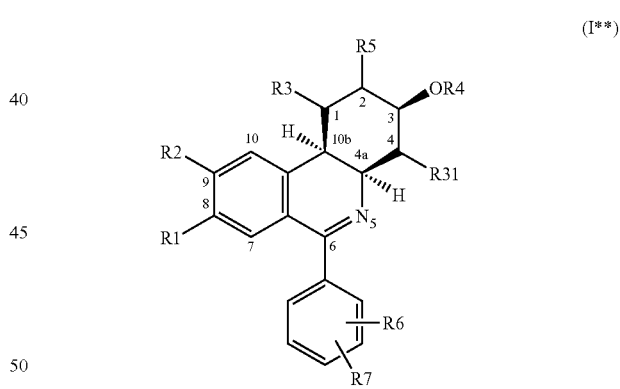

(I**)

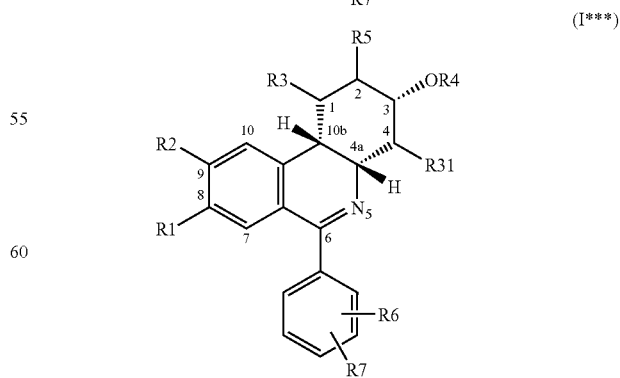

(I***)

-continued

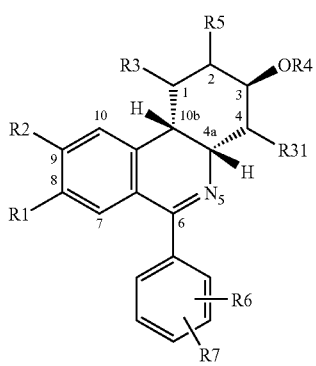

(I****)

or a salt of this compound, an N-oxide of this compound, or a salt of an N-oxide of this compound.

8. A compound of the formula I according to claim 1, which has with respect to the positions 3, 4a and 10b, the configuration shown in formula I*****:

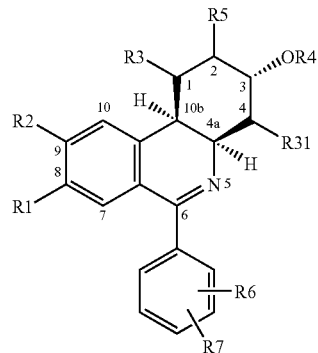

(I*****)

or a salt of this compound, an N-oxide of this compound, or a salt of an N-oxide of this compound.

9. A pharmaceutical composition comprising one or more compounds of the formula I as claimed in claim 1, or a pharmaceutically acceptable salt of this compound, a pharmaceutically acceptable N-oxide of this compound, or a salt of said N-oxide, together with a pharmaceutical auxiliary and/or excipient.

* * * * *

UNITED STATES PATENT AND TRADEMARK OFFICE
CERTIFICATE OF CORRECTION

PATENT NO. : 7,423,046 B2
APPLICATION NO. : 10/524820
DATED : September 9, 2008
INVENTOR(S) : Kautz et al.

It is certified that error appears in the above-identified patent and that said Letters Patent is hereby corrected as shown below:

Claim 1, Column 33, Line 20,
Please delete "R2 is methoxy difluoromethoxy or ethoxy,"
and
replace with
-- R2 is methoxy, difluoromethoxy or ethoxy, --

Signed and Sealed this

Fourth Day of November, 2008

JON W. DUDAS
*Director of the United States Patent and Trademark Office*